(12) United States Patent
Milmann et al.

(10) Patent No.: US 8,490,493 B2
(45) Date of Patent: Jul. 23, 2013

(54) DEVICE AND METHOD FOR THE DETECTION OF COMPOSITE DEFECTS

(75) Inventors: Boris Milmann, Berlin (DE); Rosemarie Helmerich, Berlin (DE)

(73) Assignee: Bundesanstalt fuer Materialforschung und-pruefung (BAM), Berlin (DE)

( * ) Notice: Subject to any disclaimer, the term of this patent is extended or adjusted under 35 U.S.C. 154(b) by 279 days.

(21) Appl. No.: 12/745,499

(22) PCT Filed: Nov. 24, 2008

(86) PCT No.: PCT/EP2008/066097
§ 371 (c)(1),
(2), (4) Date: Dec. 10, 2010

(87) PCT Pub. No.: WO2009/068507
PCT Pub. Date: Jun. 4, 2009

(65) Prior Publication Data
US 2011/0088472 A1 Apr. 21, 2011

(30) Foreign Application Priority Data
Nov. 30, 2007 (DE) .......................... 10 2007 057 696

(51) Int. Cl.
*G01B 17/02* (2006.01)
(52) U.S. Cl.
USPC .......................................................... 73/627
(58) Field of Classification Search
USPC .................... 73/627; 324/64.3, 63.2, 58.5
See application file for complete search history.

(56) References Cited

U.S. PATENT DOCUMENTS

| | | | | |
|---|---|---|---|---|
| 4,344,030 A | * | 8/1982 | Anderson et al. | 324/642 |
| 4,514,688 A | * | 4/1985 | Whetstone | 178/18.02 |
| 4,707,652 A | * | 11/1987 | Lowitz | 324/631 |
| 5,383,365 A | * | 1/1995 | Buttram | 73/598 |
| 5,497,100 A | * | 3/1996 | Reiser et al. | 324/643 |
| 5,619,423 A | * | 4/1997 | Scrantz | 702/51 |
| 6,142,510 A | * | 11/2000 | Endo et al. | 280/731 |
| 7,516,664 B2 | * | 4/2009 | Meier et al. | 73/644 |
| 2004/0083813 A1 | | 5/2004 | Arndt et al. | |

FOREIGN PATENT DOCUMENTS

| | | |
|---|---|---|
| DE | 195 12 176 A1 | 3/1996 |
| DE | 101 04 610 A1 | 8/2002 |
| JP | 2003-161613 A | 6/2003 |
| JP | 2005-274227 A | 10/2005 |

OTHER PUBLICATIONS

Fortunko C. M., et al "Nondestructive evaluation of planar defects in plates using low-frequency shear horizontal waves." J. Appl. Phys. vol. 53 No. 5, May 1982, pp. 3450-3458.

Su, Z. et al., "Assessment of delamination in composite beams using shear horizontal (SH) wave mode." Composites Science and Technology, Elsevier, vol. 67, No. 2, Dec. 8, 2006, pp. 244-251.

Lehmann, M. et al., "Monitoring System for Delamination Detection—Qualification of Structural health Monitoring (SHM) Systems." Conference on Damage in Composite Material CDCM 2006, Sep. 2006, Stuttgart, pp. 1-10.

* cited by examiner

*Primary Examiner* — Jewel V Thompson
(74) *Attorney, Agent, or Firm* — Sughrue Mion, PLLC

(57) ABSTRACT

Provided is a method for detecting composite defects between a first material and a second material, comprising the steps of: (a) introducing horizontally polarized low-frequency transverse waves into an upper surface of the composite material; (b) detecting an ultrasound echo of the emitted low-frequency horizontally polarized transverse waves; (c) displaying the detected ultrasound echoes on a display device.

18 Claims, 4 Drawing Sheets

FIG 3
(a)
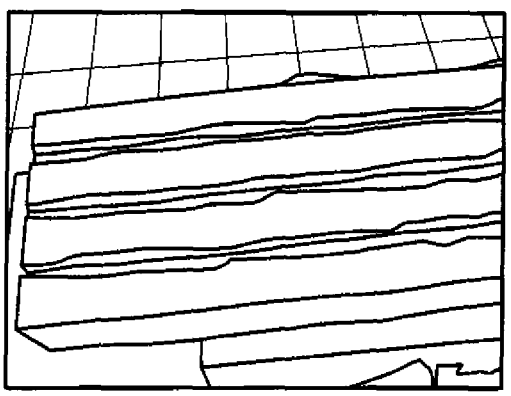
(b)
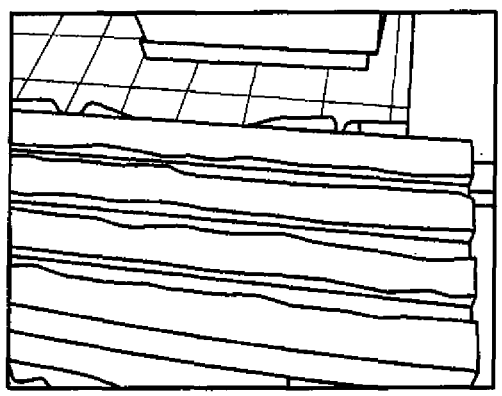
(c)
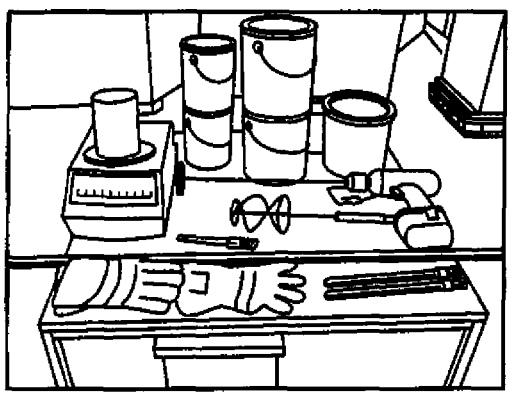
(d)
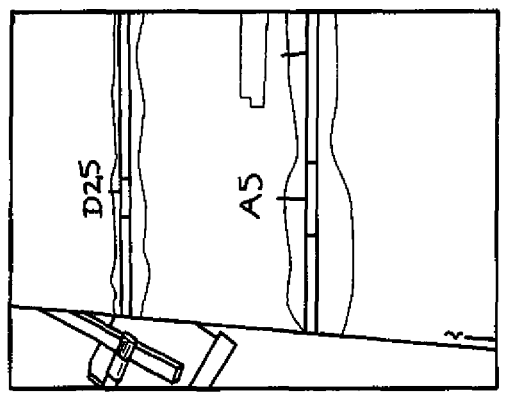
(e)
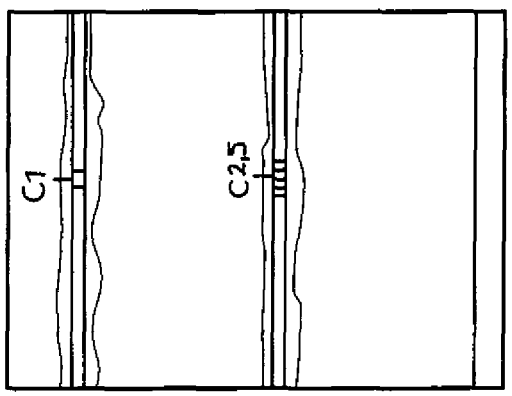
(f)
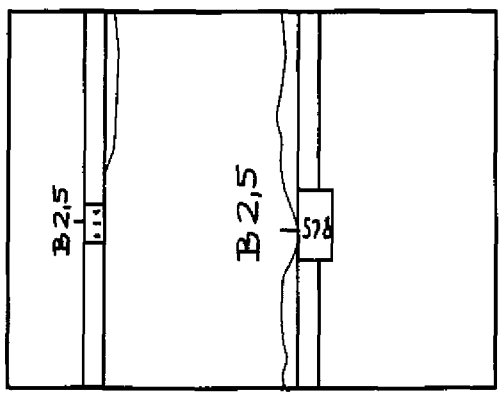

FIG 4
(a)
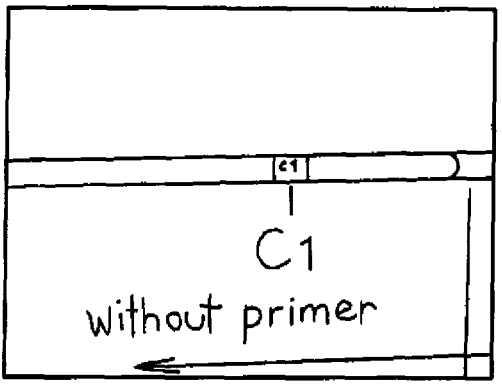
(b)
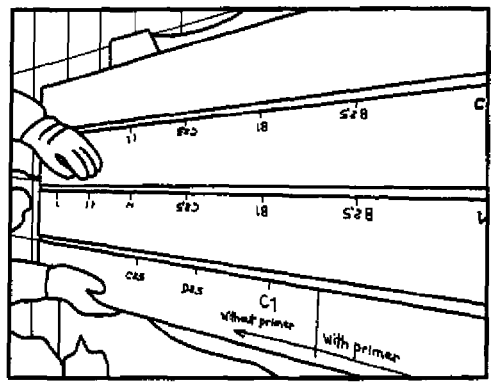
(c)
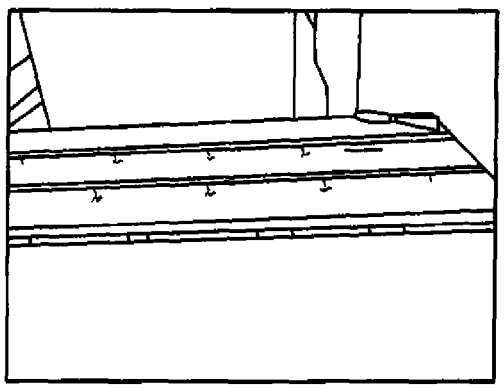
(d)
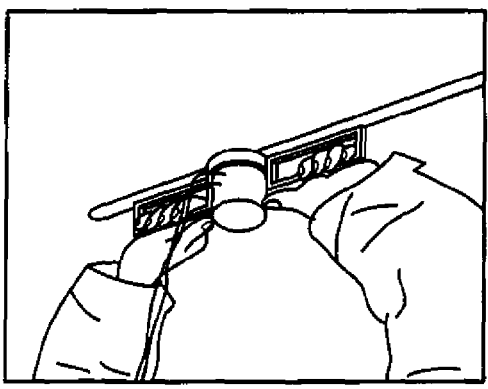
(e)
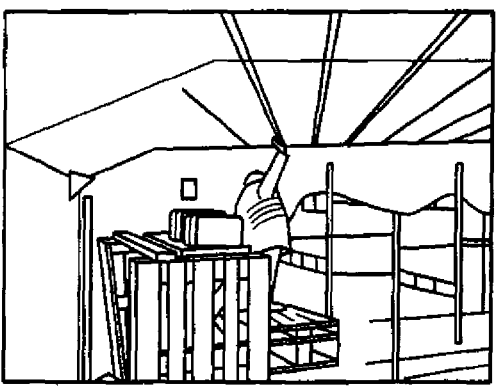
(f)

DEVICE AND METHOD FOR THE DETECTION OF COMPOSITE DEFECTS

This is a national stage entry of International Application PCT/EP2008/066097, with an international filing date of Nov. 24, 2008, which was published under PCT Article 21(2) in German, and which claims priority from DE 10 2007 057 696.1, filed Nov. 30, 2007, the complete disclosures of which are incorporated into this application by reference.

FIELD AND BACKGROUND OF THE INVENTION

The present invention relates to a device and a method for the detection of composite defects, particularly a detection of composite defects by means of ultrasound. In particular, the present invention relates to the detection of composite defects between non-metallic materials by means of ultrasound.

Composite materials are used in a very wide range of technical fields. A composite material is a material made up of two or more materials joined to one another, wherein the composite material has different material properties than its individual components. The material properties and geometry of the components and also the quality of the bond between these components are of importance for the properties of the composite materials. So, composite defects can for example lead to detachments, crack formation, poor heat conduction properties, etc. In particular, material composites of this type are to be found in the building industry. There, composite defects can for example cause a detachment of carbon fibre reinforcements such as slats and rods in slots or webs or also of plaster from a non-metallic substrate, such as for example concrete or brickwork. Particularly in the case of load bearing elements, detachments of this type can be relevant from a technical safety viewpoint.

For example, the planning of rail corridors, as well as the introduction of uniform load factors for the use of trains with axle loads of up to 30 t requires the reinforcement of numerous railway bridges in almost all European countries. Internationally, carbon-fibre reinforced plastics (CFRPs) are being used increasingly for reinforcing concrete bridges.

Only a perfect bond between the CFRP reinforcement, either realised as a slat or applied as a near-surface reinforcement in slots, guarantees maximum reinforcement effect. Some persons responsible for railway infrastructure distrust this new method of CFRP reinforcement and almost never make use of it. In order to increase trust in the new method amongst infrastructure owners and to allow the executing company the proof that the service provided by them fulfils the requirements, it is necessary to be able to clearly prove a satisfactory quality of execution of the reinforcement.

Known testing methods for the detection of detachments as well as composite defects comprise the impact echo method (tap test) by means of a manually guided wheel for example, which method is for example used in aircraft construction for detecting composite defects. A further method for the detection of composite defects is acoustic emission analysis. Particularly in the building industry, the composite has hitherto either not at all been investigated or been investigated with active infrared thermography. In the case of the hitherto favoured method of active thermography, the composite is heated and subsequently the surface temperatures on a cross sectional area of approx. 50×50 cm during a cooling time of approx. 5 min are recorded. Expensive equipment is required for the carrying out of a thermographic investigation, such as for example a thermal camera with good thermal and geometric resolution. Furthermore, during the heating, the surface of the composite material must constantly be monitored, as temperatures which are too high can possibly damage the structure of the for example epoxy-resin-bonded reinforcements. In addition, the thermography method is very tedious on account of the long cooling times. In summary, it is to be determined that in addition to the energy-intensive heating of the surfaces to be investigated, the tedious carrying out of the test and the insufficient precision during the investigation of detachments at CFRP rods in slots are definitely disadvantageous.

Furthermore, testing methods by means of ultrasound are known for composite materials. For example, the use of dry coupling ultrasound sensors for crack detection in multilayer aluminium structures is known from aircraft construction. In this case, the dry electromagnetic sending and receiving, the so-called EMUS method is used. In this case, an ultrasound wave is excited in the uppermost layer in accordance with the principle of EMUS conversion. This method cannot however be used in the case of the non-metallic materials typically used in the building industry. Frequency ranges around 100 MHz are typically used for the EMUS method. Further ultrasound testing methods make use of the acoustic impedance of the material to be tested. A comparison test specimen is however required for the characterisation of the results of such impedance-dependent methods.

With reference to that stated above, the present invention suggests a method as well as a device as recited in the independent claims. Further advantageous configurations, details, aspects and features of the present invention are apparent from the dependent claims, the description as well as the attached drawings.

BRIEF DESCRIPTION OF THE DRAWINGS

In the attached drawings:

FIGS. 3 and 4 show photographic documentation with recordings of the execution of reinforcement measures as well as a first field trial.

DETAILED DESCRIPTION OF EXEMPLARY EMBODIMENTS

Figure 1:
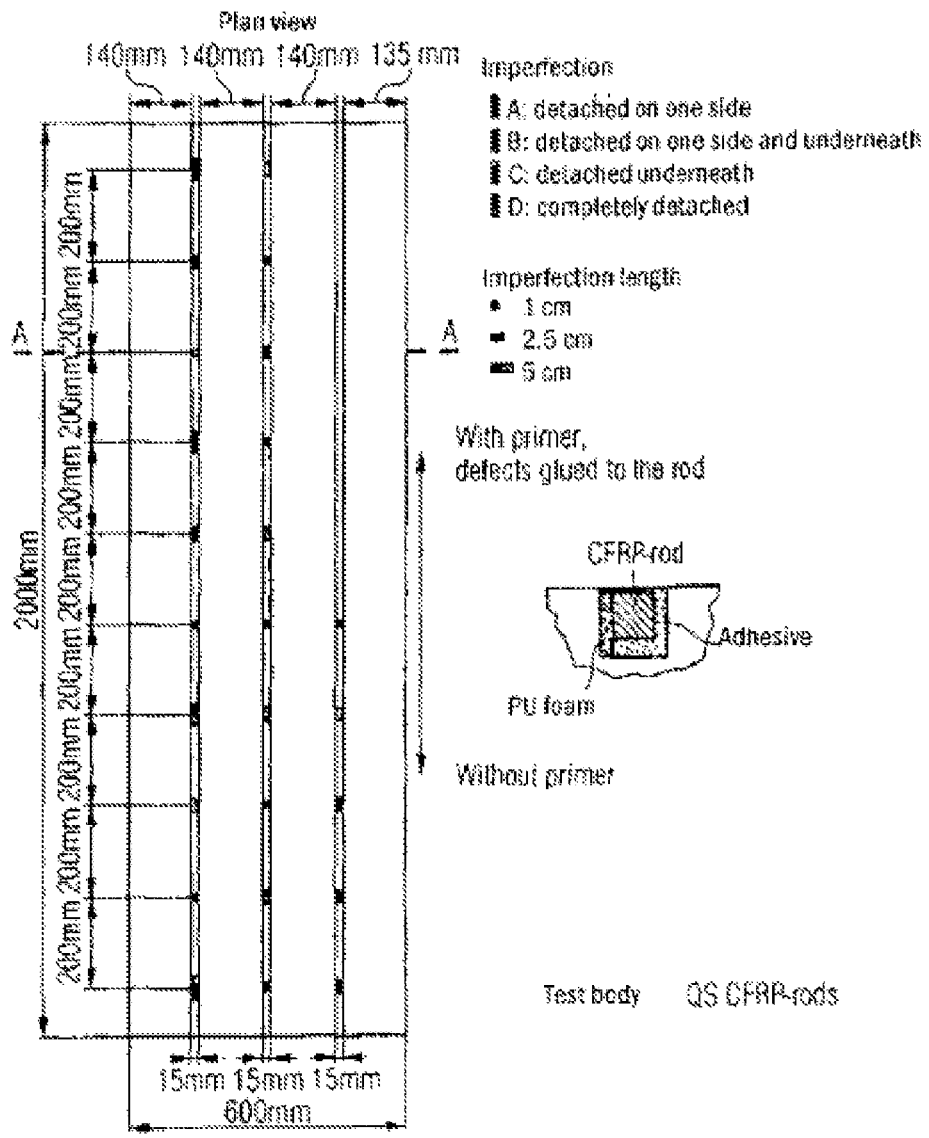
FIG. 1 shows an example for a test body with defined imperfections, which can be used for testing the device and the method according to embodiments of the present invention.

According to one exemplary embodiment of the present invention, a device for ultrasound-based detection of composite defects is provided. The device comprises dry point contact sensors which are adapted to transmit horizontally polarised low-frequency transverse waves into the uppermost layer of the composite. Typically, the device is adapted to provide an ultrasound signal with frequencies in the range from 40 to 60 kHz, particularly approximately kHz. In this case, the point contact sensors are constructed as dry coupling ultrasound transverse wave sensors. These sensors are adapted in order to transmit low-frequency horizontally polarised transverse waves, so-called SH plate waves, using transmitter/receiver echo technology into the uppermost layer of the composite. According to a development of the present invention, the above-described device can be combined with known scanning systems. In particular, the above device can be integrated into a known scanning system. According to a further embodiment, the scanning can be carried out in a fully automated manner.

According to a development, the device can comprise a plurality of dry point contact sensors. In this case, the arrangement of the plurality of dry point contact sensors with respect to one another can be adapted in such a manner that near-surface detachments are detected particularly well. In another embodiment, the arrangement of the plurality of dry point contact sensors to one another can be adapted in such a manner that deeper-located damage can be detected particularly well. According to a development, both sensor configurations can be provided in a common device in order to be able to detect both near-surface and deeper-located imperfections well.

In the case of one test method according to one exemplary embodiment of the present invention, horizontally polarised low-frequency transverse waves, so-called SH plate waves, are transmitted into the uppermost layer of the composite using transmitter/receiver echo technology by means of a suitable device, for example a device according to the above-described exemplary embodiments. Typically, the low frequency transverse waves in this case have frequencies in the range between 40 kHz and 60 kHz, particularly approximately 55 kHz. In this case, defects can be displayed immediately in the B image, that is to say the vertical section which results from the measurement curves, which are arranged in series, of the measurement points along the predetermined measurement line, on the display. After a trigger value is set initially, a signal is then present in the B image in the case of the presence of a defect, for example a composite defect, or if the composite is intact there is no signal present in the B image. In this manner, the B image gives information about the presence of an imperfection immediately in real time. So, for example, directly after the recognition of an imperfection, this can be investigated in even more detail with a denser measurement grid. According to a development of the method according to the invention, a C image, that is to say a section parallel to the surface, can subsequently be created from the B images recorded if a plurality of parallel line scans were recorded. In this manner, a composite defect which can be detected in the B scan in real time can subsequently be reconstructed three-dimensionally.

In contrast with the currently used active thermography method, in the test method according to the exemplary embodiments of the present invention, the surface of the composite does not have to be heated with energy outlay and too strong a heating of the surface is likewise ruled out.

At the same time, in contrast with EMUS conversion, the testing can be established independently of the type of the substrate, in particular non-metallic composites can be investigated. Furthermore, the described method has the advantage that it can be combined with known scanning systems and is therefore fully automatable. Likewise, the described method can be learned easily and, following a brief introduction by a person skilled in the art of ultrasound, can for example be used by a bridge inspector. Furthermore, for the testing of CFRP-reinforced reinforced concrete constructions, only a low-frequency sensor type is needed in various arrangement variants for the detection of near-surface detachments and for the detection of deeper-located damage. Finally, the described test method is more precise than the previously used thermography method. So, composite defects could be reliably detected to 1 cm$^2$.

EXAMPLE

FIG. 1 shows a test body into which defined imperfections were transmitted for testing the method according to the invention. The test body has a base body made of concrete which has a length of 2000 mm and a width of 600 mm. The base body made of concrete furthermore has three longitudinal grooves arranged parallel to one another, which in each case run across the full length of 2000 mm of the base body and in each case have a width of 15 mm. A rod made of CFRP material is adhesively bonded into a respective one of the longitudinal grooves. In this manner, a typical composite material, as is used in the reinforcement of concrete bridges with carbon-fibre reinforced plastics, is simulated.

Along the CFRP rods, composite defects are transmitted in a targeted manner as defined imperfections. In this case, both the type and the length of the imperfections vary. So, imperfections are provided in three different lengths (1 cm, 2.5 cm, 5 cm). The respective length of the imperfection can be read in FIG. 1 on the basis of the coloured bar assigned to the imperfection. Furthermore, four different types of imperfections are used. Type A designates an imperfection which is detached on one side and is characterised by a blue bar. FIG. 1 shows an imperfection of Type A in the sectional view, wherein the detached side is simulated by means of a PU foam. The imperfection of Type B is detached on one side and underneath and is characterised by a green bar. Imperfections of Type C are only detached underneath and are characterised by yellow bars. Imperfections of Type D are completely detached and are characterised by red bars.

Figure 2:
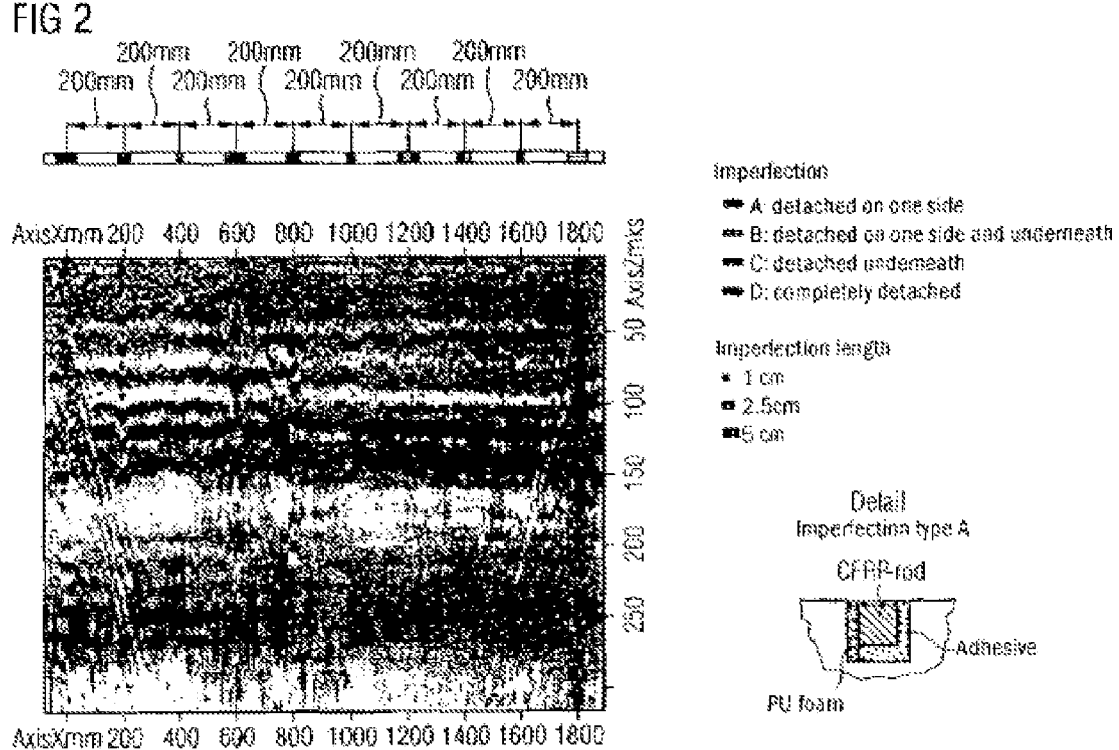
FIG. 2 shows the result of a measurement on a test body.

FIG. 2 shows the result of a measurement with the aid of the method according to the invention. In this case, the CFRP rod shown above in FIG. 2 was measured with the corresponding defined imperfections. Underneath, the recorded B images of the ultrasound measurement are shown. Therein, all imperfections of Type A as well as the imperfection of Type D can be seen clearly. Furthermore, the 2.5 cm and 5 cm sized imperfections of Type B can be seen clearly. Likewise clearly visible is the 5 cm sized imperfection of Type C. The 1 cm and 2.5 cm imperfections of Type C as well as the 1 cm sized imperfection of Type B are clearly more faintly visible than the previously described imperfections of other types. However, it can clearly be determined that the above-described method for reliable detection of 1 cm$^2$ sized composite defects is suitable.

FIG. 3 shows photographic documentation with recordings of the execution of reinforcement measures. In this case, FIGS. 3(a) and 3(b) show the test body made from concrete in which reinforcement was carried out with CFRP rods. FIGS. 3(d), 3(e) and 3(f) show the defined imperfections of various types. In FIG. 3(c) typical materials and tools are shown as they were used for the preparation of the test body.

In FIG. 4 the images (a) to (c) show further recordings of the test body. FIGS. 4(d) to 4(e) show photographic documentation with recordings of a first field trial.

The present invention was described on the basis of exemplary embodiments. These exemplary embodiments should in no way be understood as limiting for the present invention.

The invention claimed is:
1. A method for detecting defects in a composite comprising:
   transmitting, with a dry point contact sensor, horizontally polarised low frequency transverse waves into an upper layer of the composite comprising a first non-metallic material and a second non-metallic material that differs from the first non-metallic material;
   detecting an ultrasound echo of the low frequency horizontally polarised transverse waves transmitted into the composite thereby detecting a local loss of bond in the composite between the first non-metallic material and the second non-metallic material; and displaying the detected ultrasound echo on a display device, wherein the low frequency horizontally polarized transverse waves are SH plate waves.

2. The method according to claim 1, wherein the low frequency horizontally polarized transverse waves are guided ultrasound waves.

3. The method according to claim 1, wherein the frequency of the low frequency horizontally polarized transverse waves transmitted into the composite is in a range from 40 kHz to 60 kHz.

4. The method according to claim 1, wherein the frequency of the low frequency horizontally polarized transverse waves transmitted into the composite is approximately 55 kHz.

5. The method according to claim 1, wherein a B image of the composite is recorded.

6. The method according to claim 1, furthermore comprising:

generating a C image from previously recorded parallel line scans.

7. The method according to claim 1, wherein the composite comprises only non-magnetic components.

8. The method according to claim 1, wherein the composite comprises only non-metallic components.

9. A device for detecting defects in a composite comprising:

at least one dry point contact sensor which is adapted to transmit horizontally polarized low-frequency transverse waves into an uppermost layer of the composite comprising a first non-metallic material and a second non-metallic material that differs from the first non-metallic material, and a detector adapted to detect a local loss of bond in the composite between the first non-metallic material and the second non-metallic material.

10. The device according to claim 9, wherein the at least one dry point sensor is adapted to transmit SH plate waves into the uppermost layer of the composite.

11. The device according to claim 9, wherein the at least one dry point sensor comprises the detector and is adapted to transmit and to detect the horizontally polarized low frequency transverse waves using transmitter/receiver echo technology.

12. The device according to claim 9, wherein the at least one dry point sensor is adapted to transmit an ultrasound signal in a frequency range from 40 kHz to 60 kHz into the composite.

13. The device according to claim 9, wherein the at least one dry point sensor is adapted to transmit an ultrasound signal of approximately 55 kHz into the uppermost layer of the composite.

14. The device according to claim 9, wherein the device comprises a plurality of dry point contact sensors.

15. The device according to claim 14, wherein the arrangement of the plurality of dry point contact sensors with respect to one another is adapted in such a manner that near-surface detachments are detected particularly well.

16. The device according to claim 14, wherein the arrangement of the plurality of dry point contact sensors with respect to one another is adapted in such a manner that deeper-located damage is detected particularly well.

17. The method according to claim 1, wherein the composite comprises concrete structures or concrete bridges which are reinforced by carbon-fibre reinforcement plastics.

18. The device according to claim 9, wherein the composite comprises concrete structures or concrete bridges which are reinforced by carbon-fibre reinforcement plastics.

\* \* \* \* \*